United States Patent [19]

Tsuchida et al.

[11] Patent Number: 5,258,522

[45] Date of Patent: Nov. 2, 1993

[54] IMIDAZOLE-SILANE COMPOUNDS AND METAL SURFACE FINISHING AGENT CONTAINING THE SAME

[75] Inventors: Katsuyuki Tsuchida; Masashi Kumagai; Yukio Ogino, all of Toda, Japan

[73] Assignee: Nippon Mining Co., Ltd., Tokyo, Japan

[21] Appl. No.: 918,454

[22] Filed: Jul. 22, 1992

[30] Foreign Application Priority Data

Aug. 1, 1991 [JP] Japan ................ 3-214181
Jul. 10, 1992 [JP] Japan ................ 4-183783

[51] Int. Cl.$^5$ .............................................. C07F 7/02
[52] U.S. Cl. .................................................. 548/110
[58] Field of Search ........................................ 548/110

[56] References Cited

U.S. PATENT DOCUMENTS

| | | | |
|---|---|---|---|
| 4,323,689 | 4/1982 | Vogel et al. | 548/336 |
| 4,732,858 | 3/1988 | Brewer et al. | 437/228 |
| 4,950,583 | 8/1990 | Brewer et al. | 430/311 |

FOREIGN PATENT DOCUMENTS 260976  3/1988  European Pat. Off. .
2-43743  10/1990  Japan .
3-73458  11/1991  Japan .

OTHER PUBLICATIONS

A FT-IR Reflection-Absorption Spectroscopic Study of an Epoxy Coating on Imidazole-Treated Copper, Yoshida et al, J. Adhesion 1984, vol. 16, pp. 217-232.
**Chemical Abstracts, vol. 97, 1982, 97:216455c, N--Trial-koxysilylpropylimidazoles, Czech. CS 195 648.

*Primary Examiner*—Patricia L. Morris
*Attorney, Agent, or Firm*—Flynn, Thiel, Boutell & Tanis

[57] ABSTRACT

This present invention provides a novel imidazole-silane compound which has an excellent heat resistance and a high corrosion preventive effect on metal surface and is capable of remarkably improving the adhesion of a metal to a resin substrate, a process for preparing such a compound, and a new metal surface finishing agent comprising the same. The novel imidazole-silane compound is represented by the general formula (1), (2) or (3) as defined in claims and produced by reacting an imidazole compound of the general formula (4) with a 3-glycidoxypropylsilane compound of the general formula (5) at a temperature of 80° to 200° C.

1 Claim, 8 Drawing Sheets

IMIDAZOLE-SILANE COMPOUNDS AND METAL SURFACE FINISHING AGENT CONTAINING THE SAME

BACKGROUND OF THE INVENTION

1. Field of the Invention

The present invention relates to a surface finishing agent for preventing metal surfaces from corrosion or for improving adhesion, particularly a novel imidazole-silane compound useful as a surface finishing agent for copper foils usable for copper-clad laminates for printed circuits, a process for producing it, and the use thereof.

2. Description of the Relates Art

The copper-clad laminates for printed circuits are produced by laminating a copper foil to a paper substrate impregnated with a phenolic resin or a glass substrate impregnated with an epoxy resin at an elevated temperature and pressure. It is then etched to form circuit patterns and elements such as semiconductor devices or the like are mounted thereon to form circuit boards for electronic devices. In the course of this process, the copper foil has to meet various requirements, since it is adhered to the substrate, heated, immersed in an acid or alkali solution, coated with a resist ink and soldered. For instance, excellent properties, such as adhesion to the substrate, resistance to chemical attacks or the like are mainly required on one side of the copper foil to be adhered onto the substrate. This side has been roughened and is generally called "M side" (matte side; hereinafter, similarly referred to). On the other hand, the other side (opposite to the M side) which is generally called "S side" (shiny side; hereinafter similarly referred to) must have heat resistance, moisture resistance, etc. Further, it is also required of both sides of the copper foil to be free from tarnishing due to oxidation during the storage.

To satisfy these requirements, a brass layer is formed on the M side of the copper foil (see Japanese Patent Publication Nos. 35711/1976 and 6701/1979), or the M side and S side are both treated with a chromate or coated with a zinc-chromium based mixture comprising zinc or zinc oxide and chromium oxide (see Japanese Patent Publication No. 7077/1983).

Recently, with the development of high-temperature heat-resistant resin substrates, higher heat resistance has been demanded for the S side of the copper foil. For example, the S side must be free from tarnishing due to oxidation in the range of from the conventional heating conditions of 200° C.×30 minutes to higher temperature heating conditions, such as 220° C. or 240° C.×30 minutes. Also, in recent years, with a growing demand for finer patterns in printed wiring boards, further precise etching has become necessary. In order to satisfy such a demand, the M side is required to have a reduced surface roughness (i.e., low profile). However, on the other hand, roughening of the M side exhibits an anchoring effect in adhering the copper foil onto the substrate. Therefore, the requirement of low profile and the improvement in adhesion are incompatible with each other. If the anchoring effect is reduced due to low profile, the reduction of this effect should be compensated in a different manner to improve the adhesion.

It is also proposed to apply a silane coupling agent onto the M side, as a measure for strengthening the adhesion or as a countermeasure against the adhesion reduction due to the above-mentioned low profile (see Japanese Patent Publication No. 19994/1990 and Japanese Patent Laid-Open Nos. 183178/1988 and 26097/1990).

Known silane coupling agents usable for this purpose include vinyltriethoxysilane, vinyltris (2-methoxyethoxy)silane, 3methacryloxypropyltrimethoxysilane, 3glycidoxypropyltrimethoxysilane, 2-(3,4epoxycyclohexyl)ethyltrimethoxysilane, N-2-(aminoethyl)-3-aminopropyltrimethoxysilane, N-2- (aminoethyl)-3-aminopropylmethyldimethoxysilane, 3aminopropyltrimethoxy, N-phenyl-3-aminopropyltrimethoxysilane, 3-mercaptopropyltrimethoxysilane and 3-chloropropyltrimethoxysilane [see "Koubunshi tenkazai no Saishingijutsu (The Latest Techniques of Polymer Additives)", pp. 120 to 134, published by C.M.C on Jan. 6, 1988.

However, as described above, since the printed circuits are more and more densified recently, the properties required of the copper foils for the printed circuits become more and more severe.

SUMMARY OF THE INVENTION

An object of the present invention is to provide novel imidazole-silane compounds which can meet the aforesaid requirements and, more specifically, have an excellent heat resistance and a high corrosion preventive effect on a metal surface and are capable of remarkably improving the adhesion of a metal to a resin substrate, a process for preparing such compounds, and novel metal surface finishing agents comprising the same, particularly surface finishing agents for copper foils.

After intensive investigations made under these circumstances, the inventors have found that silane compounds having an certain imidazole ring not only exhibit an excellent corrosion preventive effect on metal surfaces but also remarkably improve the adhesion of a metal to a resin substrate.

The present invention has been completed on the basis of this finding.

The present invention provides:

(1) novel imidazole-silane compounds of the following general formulae (1), (2) or (3):

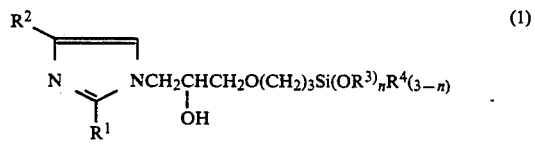

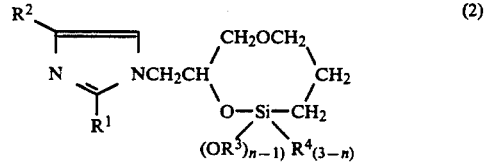

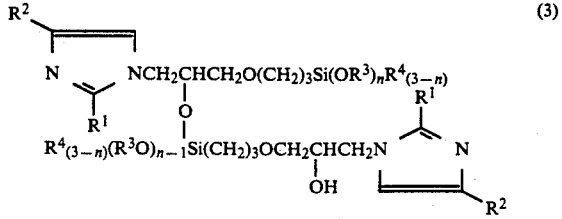

wherein $R^1$ represents hydrogen or an alkyl group having 1 to 20 carbon atoms, $R^2$ represents hydrogen, a vinyl group or an alkyl group having 1 to 5 carbon atoms, $R^3$ and $R^4$ represent an alkyl group having 1 to 3 carbon atoms and n is a number of 1 to 3.

(2) A process for producing the imidazolesilane compounds of the general formula (1), (2) or (3) as set forth above, the process comprising reacting an imidazole compound of the following general formula (4) with a 3-glycidoxypropylsilane compound of the following general formula (5) at a temperature of 80 to 200 ° C.

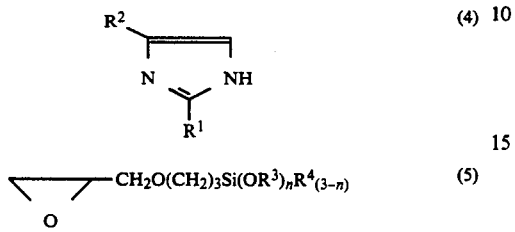

wherein $R^1$ represents hydrogen or an alkyl group having 1 to 20 carbon atoms, $R^2$ represents hydrogen, a vinyl group or an alkyl group having 1 to 5 carbon atoms, $R^3$ and $R^4$ represent an alkyl group having 1 to 3 carbon atoms and n is a number of 1 to 3.

(3) A metal surface finishing agent containing, as an effective component, at least one of the imidazole-silane compounds of the general. (1), (2) and (3) as set forth above.

(4) A surface finishing agent for copper foils which contains, as an effective component, at least one of the imidazole-silane compounds of the general formulae(1), (2) and(3) as set forth above.

DETAILED DESCRIPTION OF THE PREFERRED EMBODIMENTS

Figure 1:
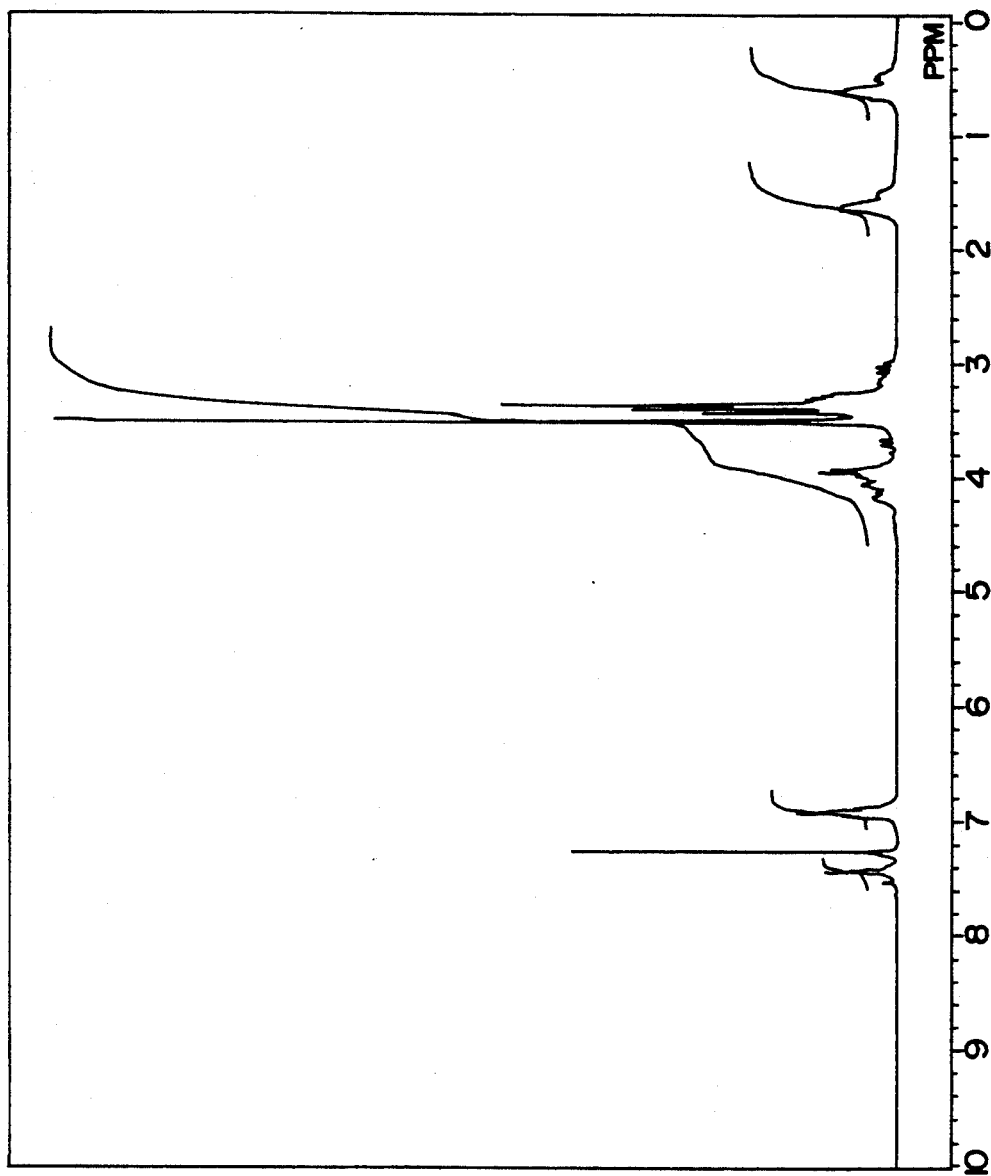
FIG. 1 is a $^1$H-NMR (nuclear magnetic resonance) spectrum of component mixture 1 obtained in Example 1 and FIG. 2 is an IR(infrared) spectrum of the same.

The present invention will be described in detail hereinafter.

$R^1$ in the above general formulae (1), (2) and (3) is hydrogen or an alkyl group having 1 to 20 carbon atoms. From the viewpoint of easiness of the synthesis, $R^1$ is preferably hydrogen or a methyl, ethyl, undecyl or heptadecyl group or the like.

$R^2$ is hydrogen, a vinyl group or an alkyl group having 1 to 5 carbon atoms. From the viewpoint of easiness of the synthesis, $R^2$ is preferably hydrogen, a methyl group or a vinyl group or the like. $R^3$ and $R^4$ are an alkyl group having 1 to 3 carbon atoms. Particularly, from the view point of easiness of the synthesis, a methyl or ethyl group is preferable as $R^3$ and $R^4$ "n" is a number of 1 to 3.

These imidazole-silane compounds of the general formulae (1), (2) and (3) according to the present invention are produced by reacting an imidazole compound represented the general formula (4) With 3-glycidoxypropylsilane compound represented by the general formula (5) at a temperature of 80° to 200° C. This reaction scheme is shown below.

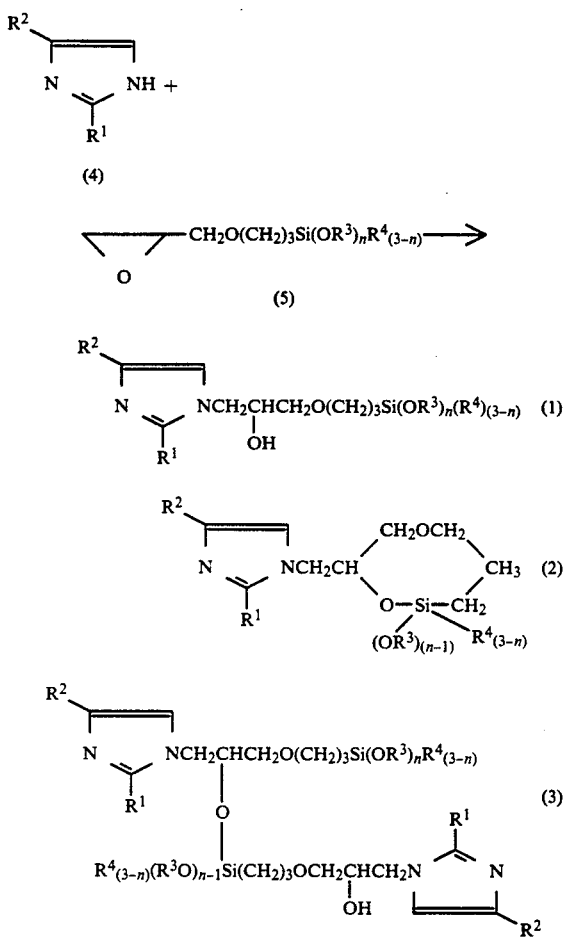

In the above formulae, $R^1$ represents hydrogen or an alkyl group having 1 to 20 carbon atoms, $R^2$ represents hydrogen, a vinyl group or an alkyl group having 1 to 5 carbon atoms, $R^3$ and $R^4$ represent an alkyl group having 1 to 3 carbon atoms and n is a number of 1 to 3.

Preferable examples of the imidazole compounds represented by the general formula (4) include imidazole, 2-alkylimidazole, 2,4-dialkylimidazole, 4-vinylimidazole, etc. Among such imidazole there may be mentioned imidazole; 2-alkylimidazole such as 2-methylimidazole, 2-ethylimidazole, 2-undecylimidazole or 2-heptadecylimidazole; or 2,4-dialkylimidazole such as 2-ethyl-4-methylimidazole or the like, as especially preferable imidazole compounds. As the 3-glycidoxypropylsilane compounds represented by the general formula (5), there may be mentioned 3-glycidoxypropylsilane, such as 3-glycidoxypropyltrimethoxysilane, 3glycidoxypropyldialkoxyalkylsilane, 3glycidoxypropylalkoxydialkylsilane, etc. Among these compounds there may be mentioned, as preferable compounds, 3-glycidoxypropyltrimethoxysilane and 3-glycidoxypropyltrimethoxysilane as 3-glycidoxypropyltrimethoxysilane; 3-glycidoxypropyldimethoxymethylsilane as 3-qlycidoxypropyldialkoxysilane; 3-glycidoxypropylethoxydimethylsilane as 3-glycidoxypropylalkoxydialkylsilane.

The reaction of the foregoing imidazole compound with 3-glycidoxypropylsilane compound is conducted preferably by adding dropwise 0.1 to 10 mol of 3-glycidoxypropylsilane compound to 1 mol of the imidazole compound heated to a temperature of 80° to 200° C. A reaction time of about 5 minutes to 2 hours is sufficient. Although no solvent is particularly necessitated for the reaction, an organic solvent such as chloroform, dioxane, methanol, ethanol or the like is usable as the reaction solvent. Since inclusion of moisture is undesirable for the reaction, it is preferably conducted in a moisture-free gas atmosphere such as a dry nitrogen or argon atmosphere so as to prevent it from being contaminated with moisture.

The imidazole-silane compounds of the above general formulae (1), (2) and (3) are produced in the state of a mixture of them by the above-mentioned reaction. These compounds can be purified and isolated by separation processes utilizing the difference in their solubilities, column chromatography or other known processes. In using these imidazole-silane compounds as metal surface finishing agents, it is not always necessary to isolate them and it is convenient and preferred to use them in the state of a mixture of them. The respective compounds of the general formulae (1), (2) and (3) in the product resulting from the above reaction are usually included in the ratio of formula (1):(2):(3)=(40 to 80):(10 to 30):(5 to 40) in terms of the area ratio by liquid chromatography analysis.

In using the imidazole-silane compounds as the metal surface finishing agent, the metals to be finished with them are not particularly limited. For instance, they are useful as surface finishing agents for copper, zinc or alloys thereof and especially suitable for use as a copper surface finishing agent. The effect of the present invention can be sufficiently exhibited particularly when the imidazole-silane compounds are used as a surface finishing agent for copper foils used in copper-clad laminates for printed circuits. The copper foils include those having a roughened surface, those having a brass layer formed thereon, chromate-treated copper foils, and those coated with a zinc-chromium based mixture.

Although at least one of the imidazole-silane compounds can be directly applied to a metal surface, it is convenient and preferred to immerse the metal in the imidazole-silane compound diluted with water; alcohol such as methanol or ethanol; or a solvent such as acetone, ethyl acetate or toluene, to a concentration of 0.001 to 20% by weight. The imidazole-silane compounds can be used either singly or in the form of a mixture of them and, if necessary, with other corrosion preventive, coupling agent, etc.

EXAMPLES

Synthesis 1 of imidazole-silane compound (Reaction of imidazole compound and 3-glycidoxypropyltrimethoxysilane)

EXAMPLE 1

3.4 g (0.05 mol) of imidazole was melted at 95° C. 11.8 g (0.05 mol) of 3-glycidoxypropyltrimethoxysilane was added dropwise thereto under stirring in an argon atmosphere for 30 minutes. After the completion of the addition, the reaction was conducted at 95° C. for additional 1 hour.

The reaction product thus obtained was in the form of a transparent, orange, viscous liquid (hereinafter referred to as the "component mixture 1").

The component mixture 1 was stably maintained in the transparent, orange, viscous liquid state for at least a few weeks without causing gelification. Further, the component mixture 1 was soluble in water, alcohol, chloroform, etc., and from the analytical results of liquid chromatography and gel permeation chromatography, it was found that the component mixture 1 was a mixture of three components.

A part of the component mixture 1 was sampled for analysis by $^1$H-NMR to find that an $>$NH peak completely disappeared and the reaction had completely proceeded. From an IR spectrum, peaks assigned to the stretching vibration of an OH group were confirmed and it was also found that the above-mentioned reaction had completely proceeded.

Figure 2:
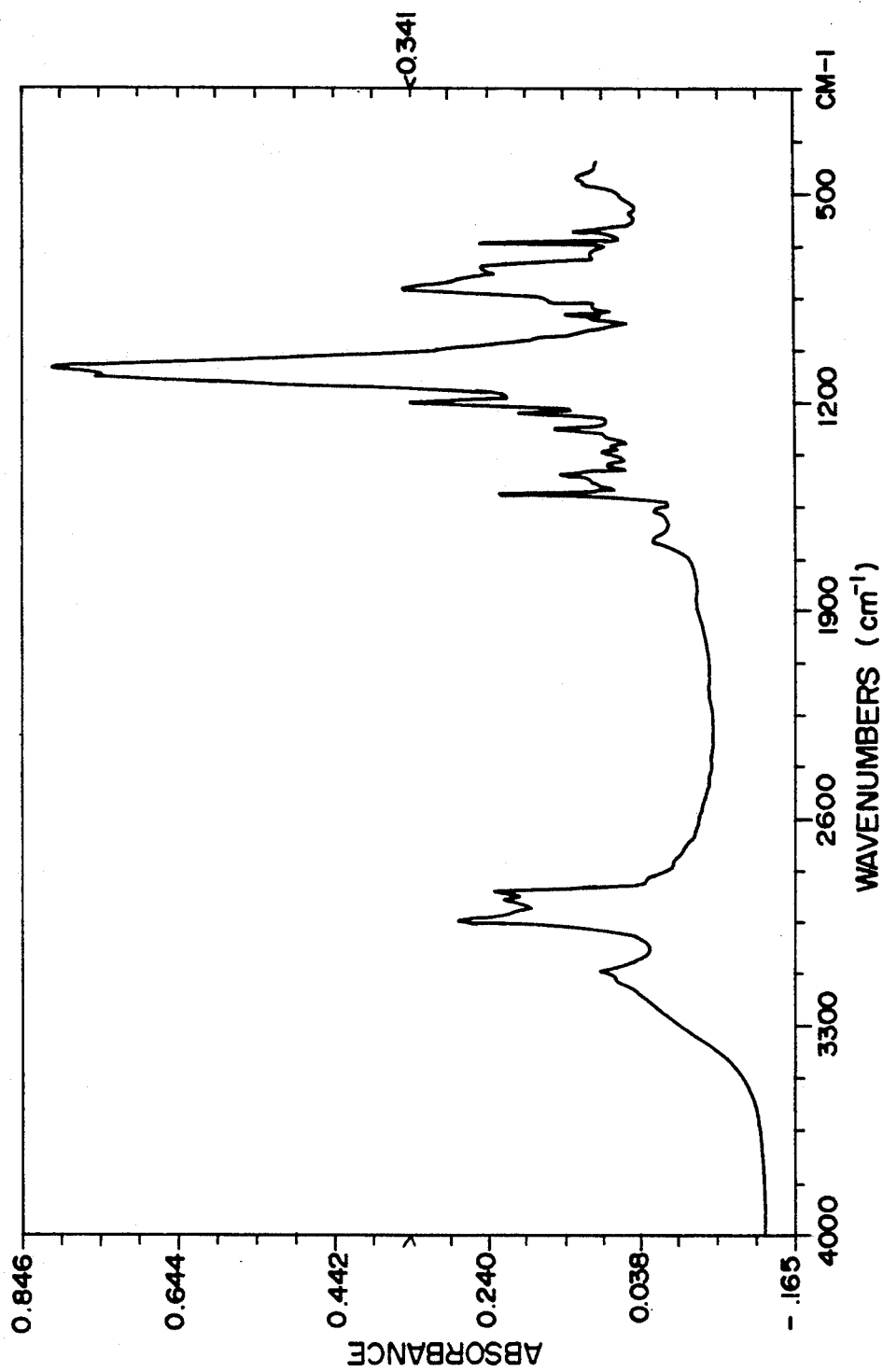

FIGS. 1 and 2 are the $^1$H-NMR spectrum and IR spectrum of the component mixture 1.

4 ml of chloroform was added to 7.5 g of the reaction product (component mixture 1) to dissolve the product, and the resultant solution was then poured into 150 ml of tetrahydrofuran. The precipitates thus formed were filtered out and the solvent was distilled off from the filtrate to obtain 4.3 g of a viscous liquid. From the analytical results of liquid chromatography and gel permeation chromatography, it was confirmed that the product was single component (hereinafter referred to as the "compound 1").

Figure 3:
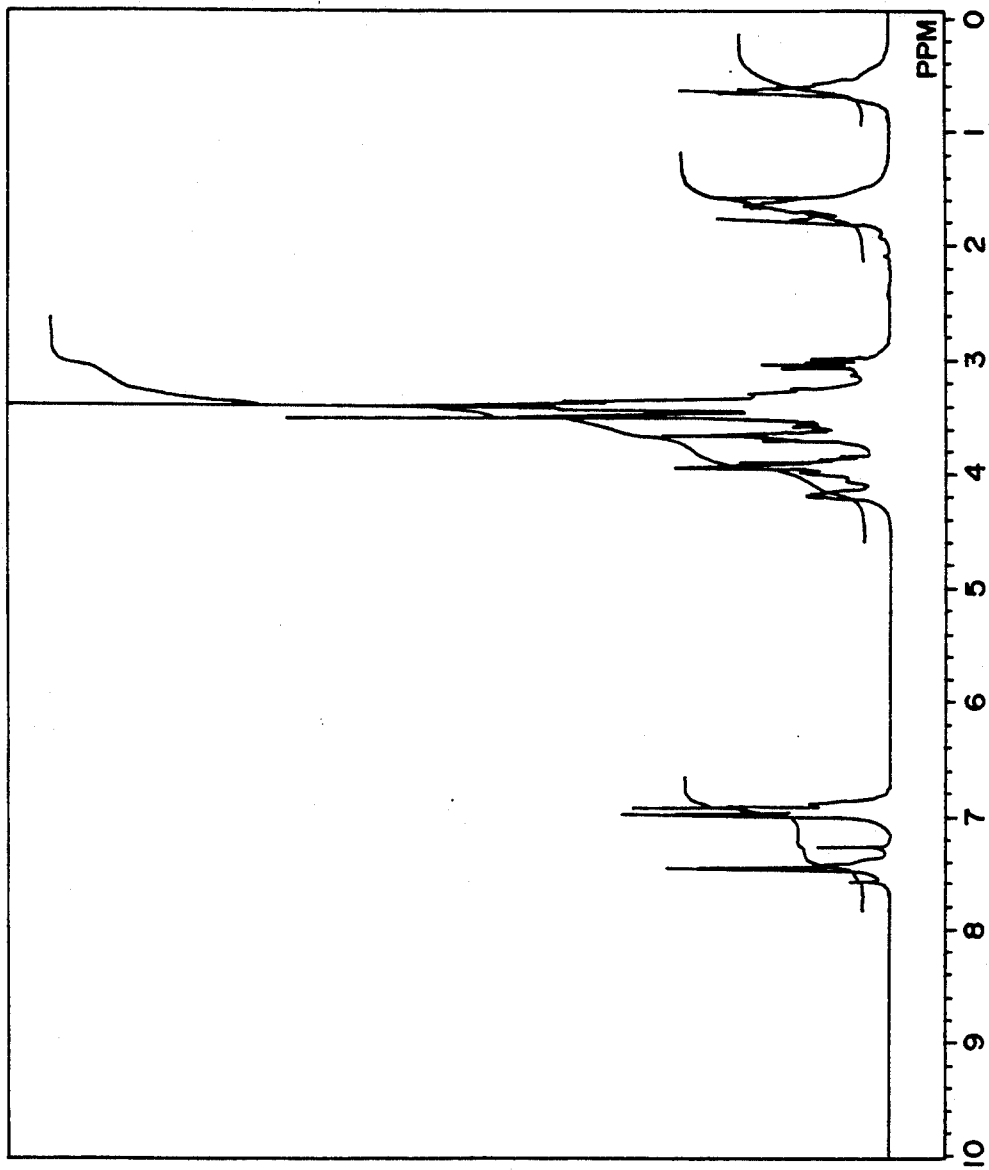
FIG. 3 is a $^1$H-NMR spectrum of compound 1 represented by the formula (2-1) in Example 1 and FIG. 4 is an IR spectrum of the same.
Figure 4:
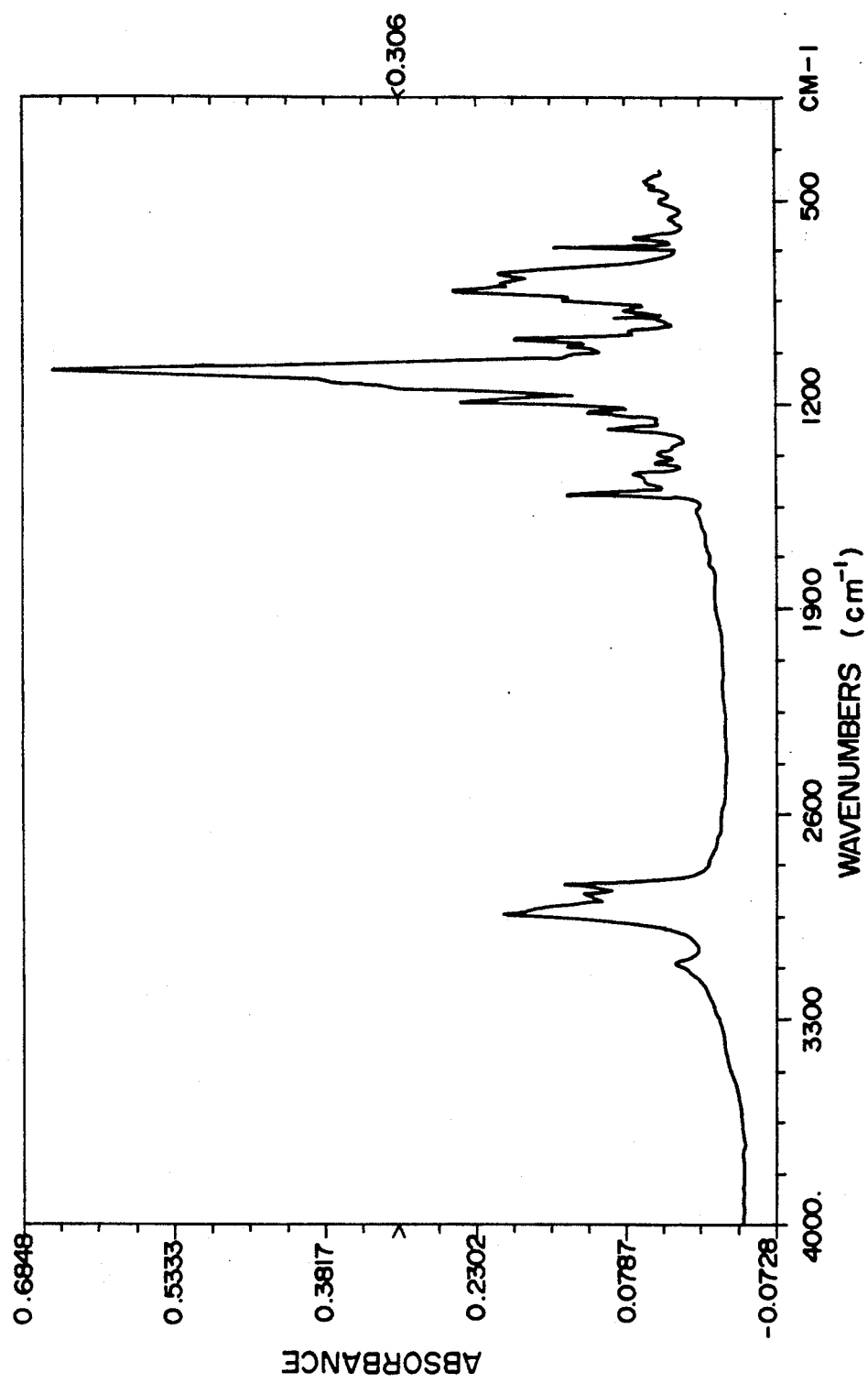

The compound 1 was subjected to $^1$H-NMR, IR and MS spectral analyses. FIGS. 3 and 4 show the $^1$H-NMR spectrum and IR spectrum of the compound 1, respectively. The results for the compound 1 are given below with the results for the component mixture 1.

Compound 1

$^1$H-NMR(CDCl$_3$, $\delta$ ppm):
0.4 to 0.7 (m, 2H), 1.5 to 1.8 (m, 2H), 2.9 to 4.3 (m, 13H), 6.93 (s, 1H), 6.95 (s, 1H), 7.44 (s, 1H)

IR (neat, cm$^{-1}$):
2940 to 2840 ($\nu_{CH}$), 1090, 810 ($\nu_{SiOMe}$)

MS: 272 (M+)

Component mixture 1

$^1$H-NMR (CDCl$_3$, $\delta$ ppm)
0.4 to 0.7 (m, 2H), 1.4 to 1.7 (m, 2H), 3.0 to 4.3 (m, 14.8H), 6.8 to 7.0 (m, 2H), 7.3 (s, 1H), 7.2 to 7.5 (m, 1H)

IR (neat, cm$^{-1}$): 3500 to 3000 ($\nu_{OH}$), 2940 to 2840 ($\nu_{CH}$), 1090, 820 ($\nu_{SiOMe}$)

It was apparent from the results that the compound I had a structure of the formula (2-1). This formula (2-1) corresponds to the general formula (2) having hydrogen as R$^1$ and R$^2$, a methyl group as R$^3$, and 3 as "n". The component mixture 1 comprised, besides the compound 1 of the formula (2-1), compounds having structures of the following formulae (1-1) and (3-1) and the mixing ratio of these three components, i.e., formula (1-1): formula (2-1): formula (3-1) was about 45:22:33 in terms of area ratio by liquid chromatography analysis using an ethanol-hexane solvent.

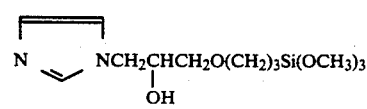
(1-1)

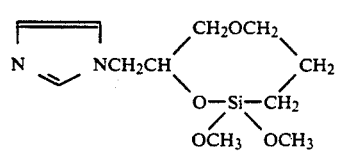
(2-1)

-continued

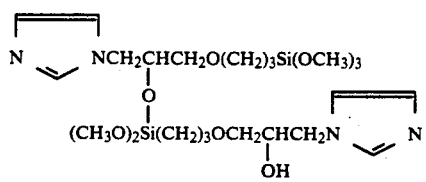

(3-1)

EXAMPLES 2 TO 7

Reactions were conducted in the same was as described in Example 1 except that the imidazole compound and reaction temperature employed in Example 1 were changed as shown in Table 1.

TABLE 1

| Ex. No. | Imidazole Compound | Reaction temperature (°C.) | Product |
|---|---|---|---|
| 2 | 2-Methylimidazole | 150 | Component mixture 2 |
| 3 | 2-Ethylimidazole | 95 | Component mixture 3 |
| 4 | 2-Ethyl-4-methylimidazole | 95 | Component mixture 4 |
| 5 | 2-Undecylimidazole | 95 | Component mixture 5 |
| 6 | 2-Heptadecylimidazole | 95 | Component mixture 6 |
| 7 | 4-Vinylimidazole | 95 | Component mixutre 7 |

The reaction products were all obtained as transparent, orange and viscous liquids. The reaction products were identified by means of $^1$H-NMR and IR as set forth in Example 1. It was confirmed that the reaction products were mixtures of compounds having structures corresponding to the foregoing general formulae (1), (2) and (3).

The imidazole-silanes (component mixtures 1 to 7 and compound 1) obtained above were evaluated as surface finishing agents for copper foils. The methods for the evaluation are as follows:

Heat resistance test

An electrolytic copper foil (75 μm thick, 4.5 cm × 4.5 cm) was degreased with acetone and then washed with a 3% aqueous sulfuric acid solution. Each of the imidazole-silane compounds of the compound 1 and component mixtures 1 to 7 was dissolved in methanol to obtain a 6 wt.% solution. The solution was spin-coated onto a shiny side of a copper foil to form a thin film of the imidazole-silane compound having a thickness of 0.3 μm.

The test pieces were heat-treated by keeping in a thermostat at each temperature of 180, 200, 220 and 240° C. for 30 minutes. For comparison, a copper foil, which had been coated with a 10 wt.% methanol solution of 3-glycidoxypropyltrimethoxysilane (hereinafter referred to merely as the "epoxysilane") available on the market as a silane coupling agent in place of the above imidazole-silane compounds to form a 0.3 μm thick coating film, and also an uncoated copper foil (hereinafter referred to as the "blank") were heat-treated in the same manner as that described above. The heat resistance was evaluated from the degree of tarnishing after the heating. The results are given in Table 2 below.

Moisture resistance test

The test pieces coated with the above-mentioned imidazole-silane compounds or the epoxysilane in the same manner as set forth above and the blank were kept in a thermo-humidistat at a temperature of 80° C. and a relative humidity of 95% for 24 hours and their moisture resistance was evaluated from the degree of the tarnishing. The results are also given in Table 2.

Adhesion test

A brass surface layer was formed on a matte side of an electrolytic copper foil (33 μm thick) and plated with a zinc-chromium based mixture consisting of zinc or zinc oxide and chromium oxide. The thus treated copper foil (25 cm × 25 cm) was immersed in a 0.4 wt.% methanol solution of each imidazole-silane compound. The foil was hung with a clip to drop a superfluous solution and, then, dried in an oven at 100° C. for 5 minutes. The matte side of each copper foil was then adhered to a substrate comprising a glass fiber cloth impregnated with an epoxy resin. The normal (room-temperature) peel strength was measured by the method of JIS C 6481. For comparison, the adhesion of a product obtained by the same treatment as that described above except that the imidazole-silane was replaced with the epoxysilane and that of a product obtained without the immersion treatment were also measured in the same way as set forth above. The results are also given in Table 2.

TABLE 2

| Finishing agent | Heat resistance | | | | Moisture resistance (80° C., 95%, 24 hr) | Adhesion peel strength (kg/cm) |
|---|---|---|---|---|---|---|
| | 180° C. | 200° C. | 220° C. | 240° C. | | |
| Blank | 2 | 2 | 1 | 1 | 1 | 2.29 |
| Epoxysilane | 3 | 2 | 2 | 1 | 1 | 2.35 |
| Component mixture 1 | 4 | 3 | 2 | 2 | 4 | 2.52 |
| Compound 1 | 4 | 3 | 2 | 2 | 3 | 2.45 |
| Component mixture 2 | 4 | 3 | 2 | 2 | 2 | 2 46 |
| Component mixture 3 | 4 | 3 | 2 | 2 | 2 | 2.47 |
| Component mixture 4 | 4 | 3 | 2 | 2 | 2 | 2.51 |
| Component mixture 5 | 4 | 3 | 2 | 2 | 4 | 2.49 |
| Component mixture 6 | 4 | 3 | 3 | 2 | 4 | 2.43 |
| Component mixture 7 | 4 | 3 | 2 | 2 | 5 | 2.35 |

Heat and Moisture resistance tests:
5: no tarnishing,
4: very slight tarnishing,
3: slight tarnishing,
2: color change into orange or yellow,
1: color change into dark brown

EXAMPLES 8-10

Synthesis 2 of imidazole-silane compound (Reaction of imidazole compound and 3-glycidoxypropyltrimethoxysilane)

Reactions were conducted in the same way as described in Example 1 except that the imidazole compound and reaction temperature set forth in Example 1 were changed as shown in Table 3 and 3-glycidoxypropyltrimethoxysilane was used as the 3-glycidoxypropylsilane compound.

TABLE 3

| Ex. No. | Imidazole Compound | Reaction temperature (°C.) | Product |
|---|---|---|---|
| 8 | Imidazole | 95 | Component mixture 9 |
| 9 | 2-Ethyl-4-methylimidazole | 95 | Component mixture 9 |
| 10 | 2-Undecylimidazole | 95 | Component mixture 10 |

The reaction products were all obtained as transparent, orange and viscous liquids. The reaction products were identified by $^1$H-NMR and IR as set forth in Example 1. It was confirmed that the reaction products were mixtures of compounds having structures corresponding to the foregoing general formulae (1), (2) and (3).

The thus produced imidazole-silanes (component mixtures 8 to 10) were each applied onto the surface of a copper foil as a surface finishing agent in the same way as described in Examples 1 to 7 and evaluated. The shiny side of each of the thus surface-treated copper foils was examined for its heat resistance and moisture resistance and the matte side was examined for its adhesion in the same manner as described in Examples 1 to 7. The results are shown in Table 4.

TABLE 4

| Finishing agent | Heat resistance | | | | Moisture resistance (80° C., 95%, 24 hr) | Adhesion peel strength (kg/cm) |
|---|---|---|---|---|---|---|
| | 180° C. | 200° C. | 220° C. | 240° C. | | |
| Blank | 2 | 2 | 1 | 1 | 1 | 2.24 |
| Epoxysilane | 3 | 2 | 2 | 1 | 1 | 2.26 |
| Component mixture 8 | 4 | 3 | 2 | 2 | 4 | 2.43 |
| Component mixture 9 | 4· | 3 | 2 | 2 | 4 | 2.44 |
| Component mixture 10 | 4 | 3 | 2 | 2 | 5 | 2.40 |

Heat and Moisture resistance tests:
5: no tarnishing,
4: very slight tarnishing,
3: slight tarnishing,
2: color channge into orange or yellow,
1: color change into dark brown

EXAMPLES 11–14

Synthesis 3 of imidazole-silane compound (Reaction of imidazole compound and 3-glycidoxypropyldimethoxymethylsilane)

Reactions were conducted in the same way as described in Example 1 except that the imidazole compound and reaction temperature set forth in Example 1 were changed as shown in Table 5 and 3-glycidoxypropyldimethoxymethylsilane was used as the 3-glycidoxypropylsilane compound.

TABLE 5

| Ex. No. | Imidazole Compound | Reaction temperature (°C.) | Product |
|---|---|---|---|
| 11 | Imidazole | 95 | Component mixture 11 |
| 12 | 2-Methylimidazole | 150 | Component mixture 12 |
| 13 | 2-Ethylimidazole | 95 | Component mixture 13 |

TABLE 5-continued

| Ex. No. | Imidazole Compound | Reaction temperature (°C.) | Product |
|---|---|---|---|
| 14 | 2-Ethyl-4-methylimidazole | 95 | Component mixture 14 |

The reaction products were all obtained as transparent, orange and viscous liquids. The reaction products were identified by $^1$H-NMR and IR spectral analyses as set forth in Example 1. It was confirmed that the reaction products were mixtures of compounds having structures corresponding to the foregoing general formulae (1), (2) and (3).

Figure 5:
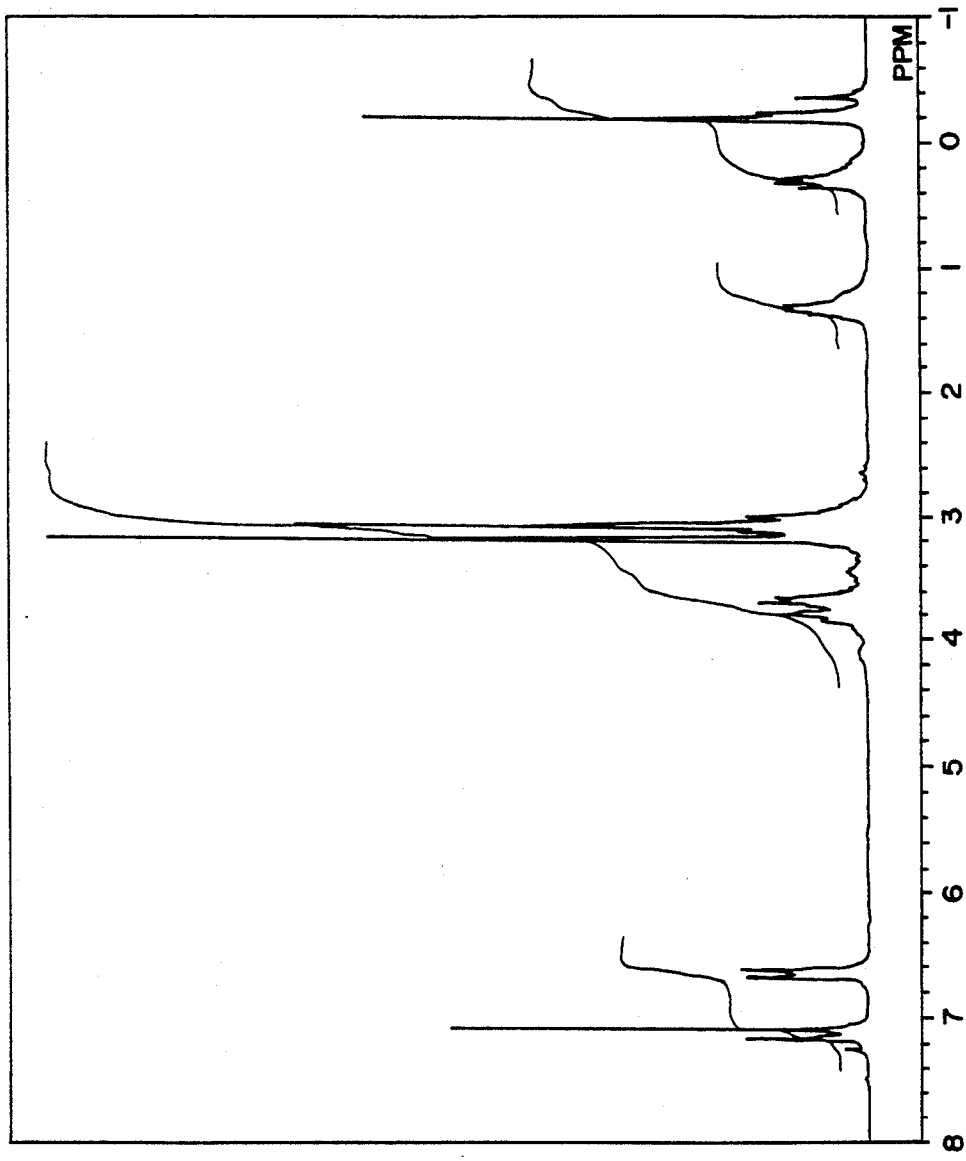
FIG. 5 is a $^1$H-NMR spectrum of component mixture 11 obtained in Example 11 and FIG. 6 is an IR spectrum of the same.
Figure 6:
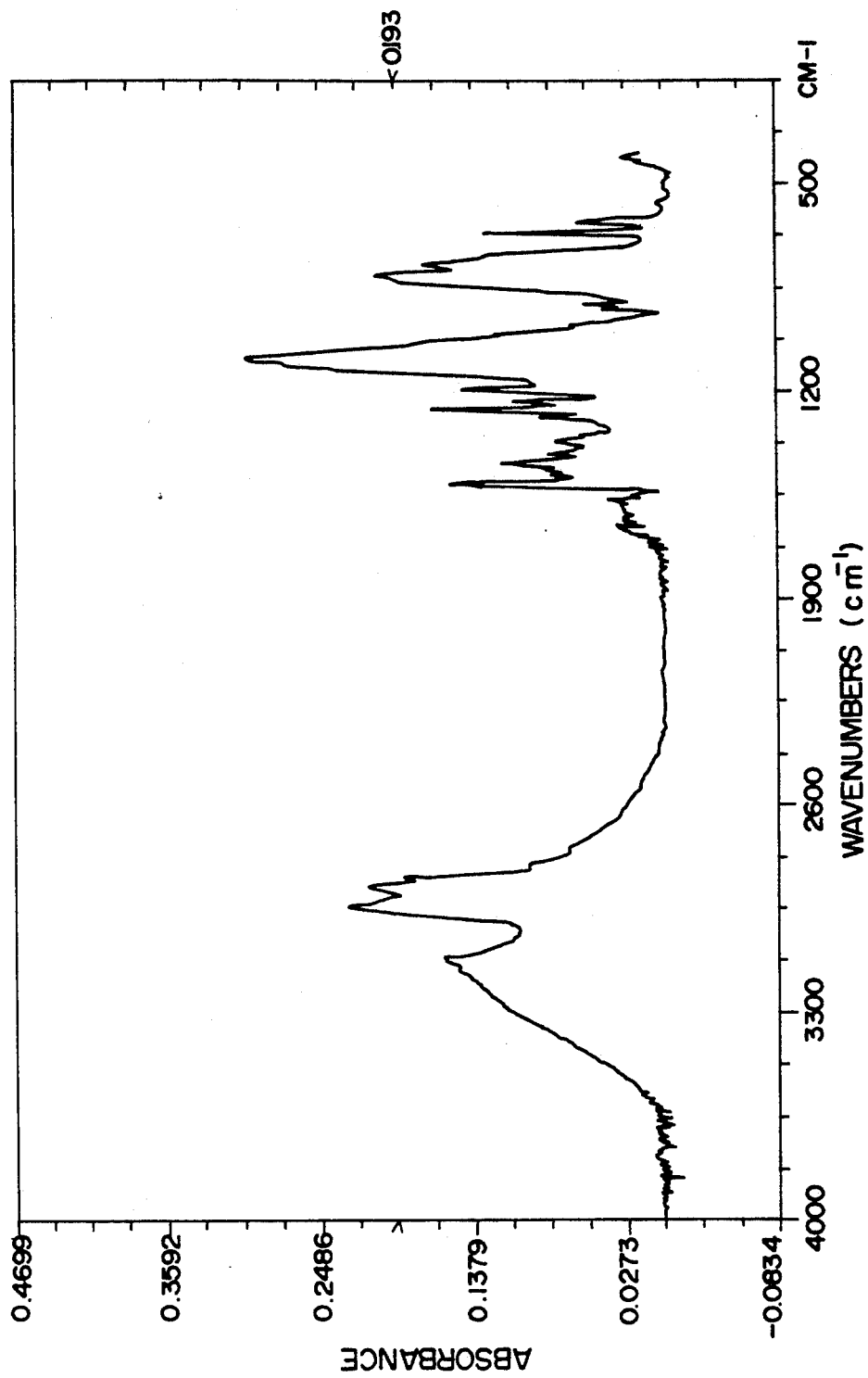

FIGS. 5 and 6 show the $^1$H-NMR spectrum and IR spectrum of the component mixture 11, respectively. The analytical results are given below.

1H-NMR (CDC13, δ ppm):
−0.2 (s, 3H), 0.1 to 0.4 (m, 2H), 1.1 to 1.4 (m, 2H),
2.9 to 3.3 (m, 8H), 3.6 to 3.9 (m, 3H), 6.6 (s, 1H),
6.7 (s, 1H), 7.1 (s, 1H), 7.2 (s, 1H)

IR (neat, cm$^{-1}$):
3600 to 3000 ($\nu_{OH}$), 2940 to 2830 ($\nu_{CH}$), 1260 (δ $CH_{(SiMe)}$)1090, 815 ($\nu_{SiOMe}$), 780 ($\nu_{SiC(SiMe)}$)

The imidazole-silanes (component mixtures 11 to 14) were applied onto the surfaces of copper foils as surface finishing agents in the same way as described in Examples 1 to 7 and evaluated. The shiny side of each copper foil was examined for its heat resistance and the matte side was examined for its adhesion in the same manner as described in Examples 1 to 7. The results are shown in Table 6.

TABLE 6

| Finishing agent | Heat resistance | | | | Adhesion peel strength (kg/cm) |
|---|---|---|---|---|---|
| | 180° C. | 200° C. | 220° C. | 240° C. | |
| Blank | 2 | 2 | 1 | 1 | 2.24 |
| Epoxysilane | 3 | 2 | 2 | 1 | 2.26 |
| Component mixture 11 | 4 | 3 | 2 | 2 | 2.41 |
| Component mixture 12 | 4 | 3 | 2 | 2 | 2.48 |
| Component mixture 13 | 3 | 3 | 2 | 2 | 2.34 |
| Component mixture 14 | 4 | 3 | 2 | 2 | 2.32 |

Heat resistance test:
5: no tarnishing,
4: very slight tarnishing,
3: slight tarnishing,
2: color change into orange or yellow,
1: color change into dark brown Examples 15–17

Synthesis 4 of imidazole-silane compound: (Reaction of imidazole compound and 3-glycidoxypropylethoxydimethylsilane)

Reactions were conducted in the same way as described in Example 1 except that the imidazole compound and reaction temperature set forth in Example 1 were changed as shown in Table 7 and 3-glycidoxypropylethoxydimethylsilane was used as the 3-glycidoxypropylsilane compound.

TABLE 7

| Ex. No. | Imidazole Compound | Reaction temperature (°C.) | Product |
| --- | --- | --- | --- |
| 15 | Imidazole | 95 | Component mixture 15 |
| 16 | 2-Ethyl-4-methylimidazole | 95 | Component mixture 16 |
| 17 | 2-Undecylimidazole | 95 | Component mixture 17 |

The reaction products were all obtained as transparent, orange and viscous liquids. The reaction products were identified by $^1$H-NMR and IR as set forth in Example 1. It was confirmed that the reaction products were mixtures of compounds having structures corresponding to the foregoing general formulae (1), (2) and (3).

The mixing ratio of the compounds, general formula (1) : general formula (2) : general formula (3), of the product (component mixture 15) obtained in Example 15 was 73 : 19 : 8 in terms of the area ratio by gel permeation chromatography using THF as a solvent.

Figure 7:
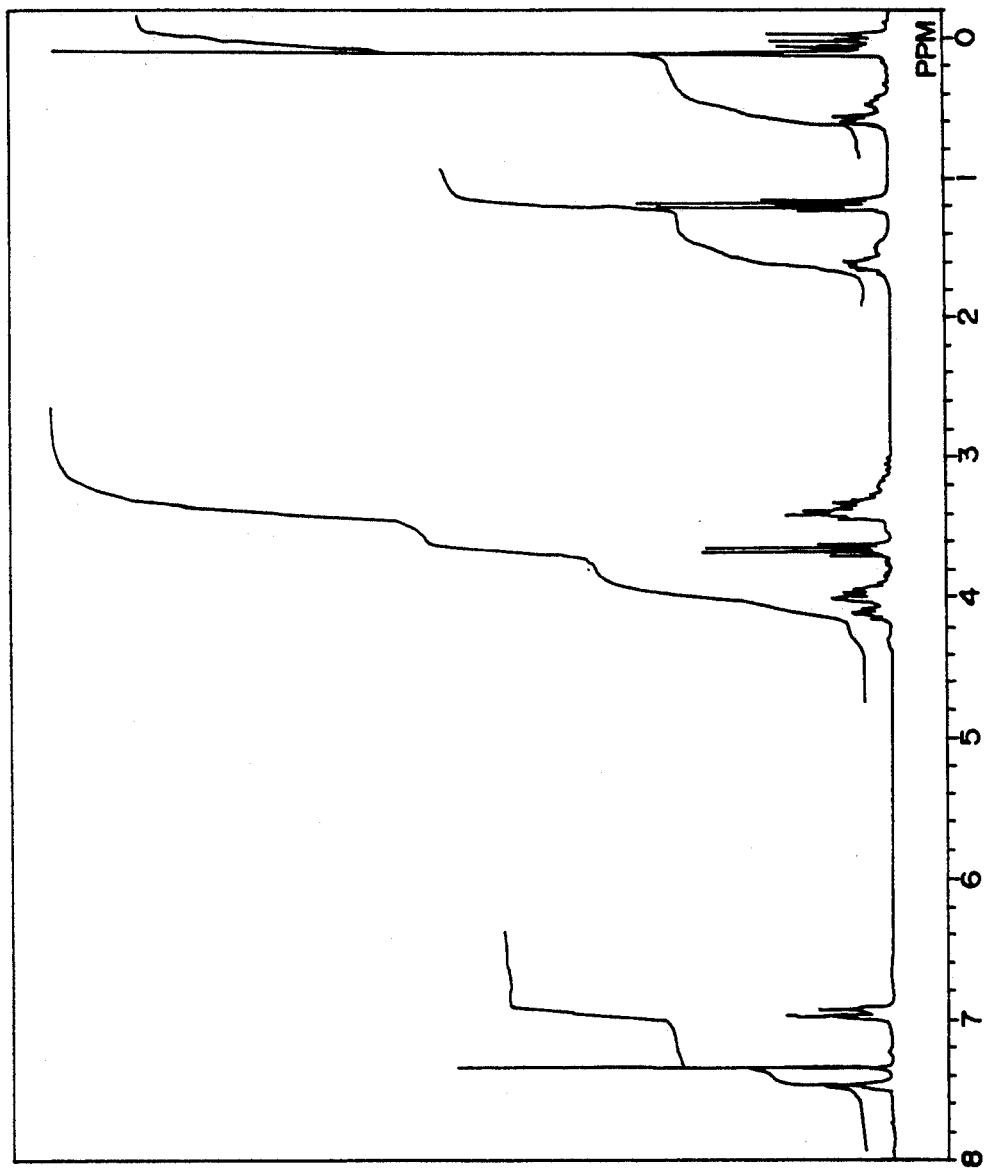
FIG. 7 is a $^1$H-NMR spectrum of component mixture 15 obtained in Example 15 and FIG. 8 is an IR spectrum of the same.
Figure 8:
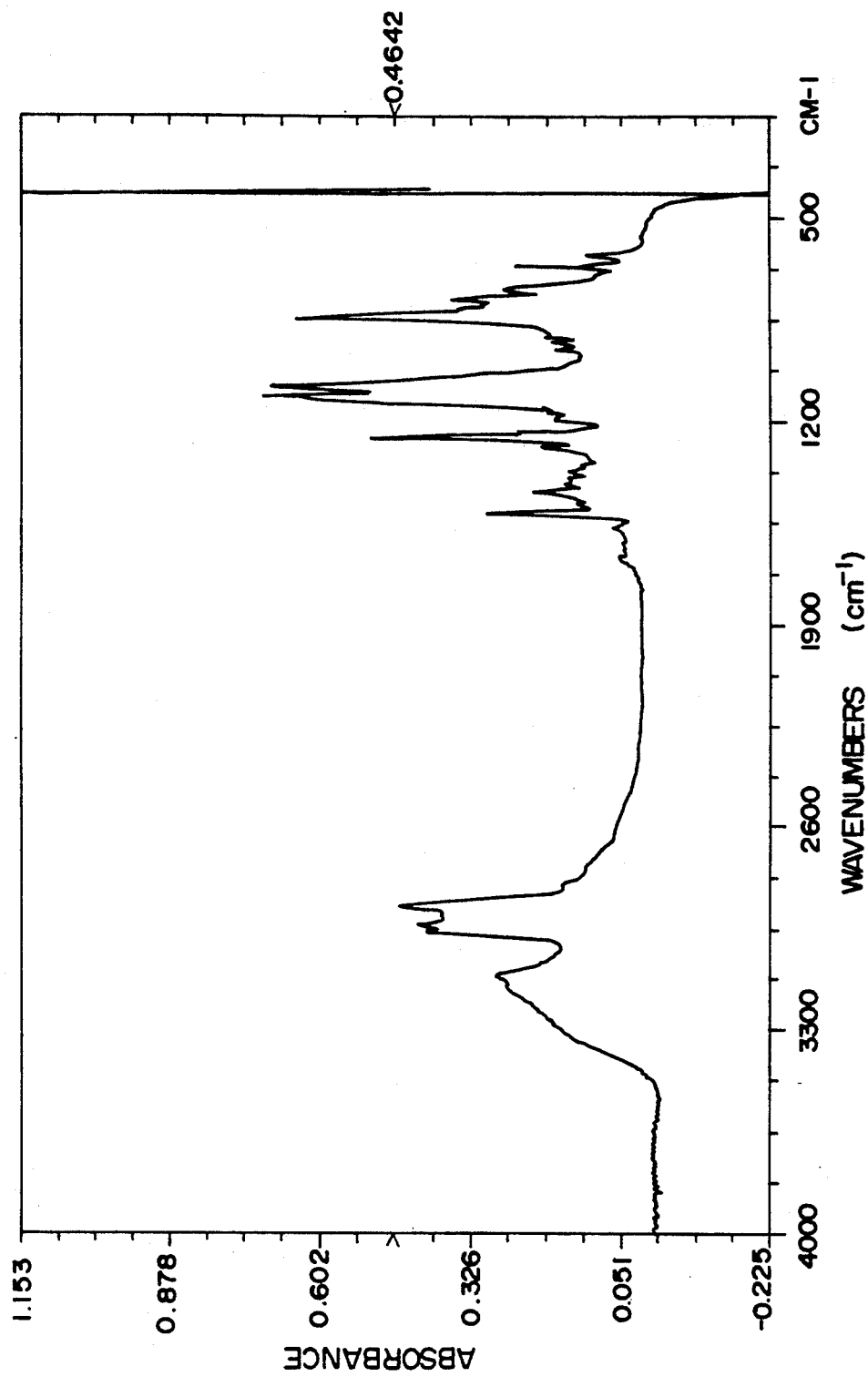

FIGS. 7 and 8 show the $^1$H-NMR spectrum and IR spectrum of the component mixture 15, respectively. The results are given below.

$^1$H-NMR (CDCl$_3$, δ ppm):
0 to 0.1 (m, 6H), 0.4 to 0.7 (m, 2H), 1.1 to 1.3 (m, 3H), 1.4 to 1.7 (m, 2H), 3.2 to 3.5 (m, 4H), 3.6 to 3.7 (q, 2H), 3.9 to 4.2 (m, 3H), 6.9 (s, 1H), 7.0 (s, 1H), 7.3 (s, 1H), 7.5 (s, 1H)

IR (neat, cm$^{-1}$):
3500 to 3000 ($\nu_{OH}$), 2950 to 2850 ($\nu_{CH}$), 1255 (δ $_{CH(SiMe)}$), 1110, 1090 ($\nu_{SiOEt}$), 805, 780 ($\nu_{SiC(SiMe)}$)

The imidazole-silanes (component mixtures 15 to 17) were applied onto the surfaces of copper foils as surface finishing agents in the same way as described in Examples 1 to 7 and evaluated. The shiny side of each copper foil was examined for its heat resistance in the same manner as described in Examples 1 to 7. The results are shown in Table 8.

TABLE 8

| Finishing agent | Heat resistance | | | |
| --- | --- | --- | --- | --- |
| | 180° C. | 200° C. | 220° C. | 240° C. |
| Blank | 2 | 2 | 1 | 1 |
| Epoxysilane | 3 | 2 | 2 | 1 |
| Component mixture 15 | 3 | 3 | 2 | 2 |
| Component mixture 16 | 3 | 3 | 2 | 2 |
| Component mixture 17 | 3 | 2 | 2 | 2 |

Heat resistance test:
5: no tarnishing,
4: very slight tarnishing,
3: slight tarnishing,
2: color change into orange or yellow,
1: color change into dark brown From the results, it is apparent that the compounds of the present invention have excellent heat resistance, corrosion preventive effect, adhesion-improving effect and any others.

The novel imidazole-silane compounds of the present invention are useful as a metal surface finishing agent, particularly as a surface finishing agent for copper foils. They have excellent heat resistance and corrosion preventive effect for a metal and are capable of remarkably improving the adhesion of a metal to a resin substrate.

What is claimed:

1. An imidazole-silane compound of the following formulae (1), (2) or (3):

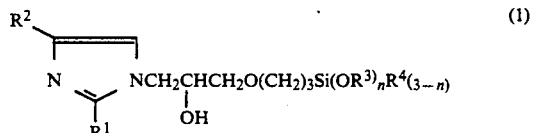

(1)

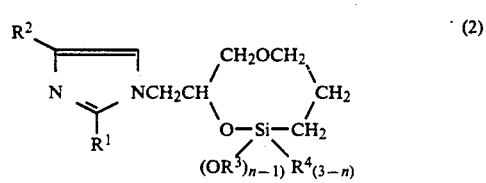

(2)

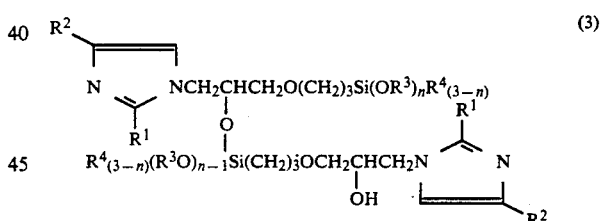

(3)

wherein R$^1$ represents hydrogen or an alkyl group having 1 to 20 carbon atoms, R$^2$ represents hydrogen, a vinyl group or an alkyl group having 1 to 5 carbon atoms, R$^3$ and R$^4$ represent an alkyl group having 1 to 3 carbon atoms and n is a number of 1 to 3.

* * * * *